(12) United States Patent
Ghannoum (10) Patent No.: US 8,545,462 B2
(45) Date of Patent: Oct. 1, 2013

(54) PATCH FOR IRRIGATION/ASPIRATION TIP

(75) Inventor: Ziad R. Ghannoum, Trabuco Canyon, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 436 days.

(21) Appl. No.: 12/616,544

(22) Filed: Nov. 11, 2009

(65) Prior Publication Data

US 2011/0112471 A1     May 12, 2011

(51) Int. Cl.
*A61M 35/00*     (2006.01)
*A61M 1/00*     (2006.01)
*A61M 3/00*     (2006.01)
*A61F 9/00*     (2006.01)

(52) U.S. Cl.
USPC ............... 604/294; 604/27; 604/43; 606/107

(58) Field of Classification Search
USPC ............... 604/22, 27, 43, 300, 294, 528, 302, 604/35, 39, 295, 297, 274, 170.01, 121, 521, 604/118, 23, 40, 42; 606/107, 5, 4
See application file for complete search history.

(56) References Cited

U.S. PATENT DOCUMENTS

| | | | |
|---|---|---|---|
| 3,805,787 A | 4/1974 | Banko |
| 4,014,333 A | 3/1977 | McIntyre |
| 4,047,532 A | 9/1977 | Phillips et al. |
| 4,204,328 A | 5/1980 | Kutner |
| 4,445,509 A | 5/1984 | Auth |
| 4,487,600 A | 12/1984 | Brownlie et al. |
| 4,531,943 A | 7/1985 | Van Tassel et al. |
| 4,573,979 A | 3/1986 | Blake |
| 4,652,255 A | 3/1987 | Martinez |
| 4,710,180 A | 12/1987 | Johnson |
| 4,717,387 A | 1/1988 | Inoue et al. |
| 4,813,926 A | 3/1989 | Kerwin |
| 4,878,900 A | 11/1989 | Sundt |

(Continued)

FOREIGN PATENT DOCUMENTS

| | | |
|---|---|---|
| DE | 197 00 809 A | 7/1998 |
| EP | 0778 039 A1 | 6/1997 |
| FR | 2713492 A1 | 6/1995 |
| WO | WO 2010/056448 A1 | 5/2010 |

OTHER PUBLICATIONS

ALCON Laboratories, Inc., "You have a choice: The ALCON Silicone I/A Tip," 2007, 2 pages.

(Continued)

*Primary Examiner* — Nicholas Lucchesi
*Assistant Examiner* — Brooke Matney (57) ABSTRACT

In various embodiments, an ophthalmic surgical instrument may include an aspiration tube, an irrigation/aspiration tip (formed of a first material such as plastic), and a patch, coupled to the irrigation/aspiration tip, made of a second material (e.g., silicone) having a higher coefficient of friction than the first material. In some embodiments, the patch may be placed on the irrigation/aspiration tip in a position to allow a user of the irrigation/aspiration tip to manipulate an intraocular lens (IOL) through contact between the patch and the IOL. For example, the patch may be positioned on a side of the irrigation/aspiration tip opposite an aspiration port or on a distal end of the irrigation/aspiration tip. In some embodiments, the patch may be formed separately and coupled to the irrigation/aspiration tip through an adhesive or may be molded onto the irrigation/aspiration tip. In some embodiments, the patch may include features to increase friction.

18 Claims, 8 Drawing Sheets

(56) References Cited

U.S. PATENT DOCUMENTS

| | | |
|---|---|---|
| 4,897,079 A | 1/1990 | Zaleski et al. |
| 4,904,238 A | 2/1990 | Williams |
| 4,921,482 A | 5/1990 | Hammerslag et al. |
| 4,983,160 A | 1/1991 | Steppe et al. |
| 4,998,916 A | 3/1991 | Hammerslag et al. |
| 4,998,923 A | 3/1991 | Samson et al. |
| 5,037,391 A | 8/1991 | Hammerslag et al. |
| 5,084,009 A | 1/1992 | Mackool |
| 5,084,012 A | 1/1992 | Kelman |
| 5,106,381 A | 4/1992 | Chikama |
| 5,108,368 A | 4/1992 | Hammerslag et al. |
| 5,133,159 A | 7/1992 | Nelson |
| 5,151,084 A | 9/1992 | Khek |
| 5,176,126 A | 1/1993 | Ckikama |
| 5,203,772 A | 4/1993 | Hammerslag et al. |
| 5,217,465 A | 6/1993 | Steppe |
| 5,224,950 A * | 7/1993 | Prywes ............... 606/166 |
| 5,242,449 A | 9/1993 | Zaleski |
| 5,286,256 A | 2/1994 | Mackool |
| 5,290,892 A | 3/1994 | Namdaran et al. |
| 5,292,310 A | 3/1994 | Yoon |
| 5,308,324 A | 5/1994 | Hammerslag et al. |
| 5,358,507 A | 10/1994 | Daily |
| 5,364,405 A | 11/1994 | Zaleski |
| 5,372,587 A | 12/1994 | Hammerslag et al. |
| 5,378,234 A | 1/1995 | Hammerslag et al. |
| 5,381,782 A | 1/1995 | Delarama et al. |
| 5,403,901 A | 4/1995 | Namdaran et al. |
| 5,421,955 A | 6/1995 | Lau et al. |
| 5,433,746 A | 7/1995 | Namdaran et al. |
| 5,441,496 A | 8/1995 | Easley et al. |
| 5,514,086 A | 5/1996 | Parisl et al. |
| 5,522,826 A | 6/1996 | Daily |
| 5,603,710 A | 2/1997 | Easley et al. |
| 5,645,530 A | 7/1997 | Boukhny et al. |
| 5,693,062 A | 12/1997 | Stegmann et al. |
| 5,718,677 A | 2/1998 | Capetan et al. |
| 5,836,926 A | 11/1998 | Peterson et al. |
| 5,873,851 A | 2/1999 | Nilsson |
| 5,921,998 A | 7/1999 | Tano et al. |
| 5,957,928 A | 9/1999 | Kirwan |
| 6,068,641 A | 5/2000 | Varsseveld |
| 6,132,426 A | 10/2000 | Kroll |
| 6,224,467 B1 * | 5/2001 | Tanaka et al. ............... 451/42 |
| 6,340,355 B1 | 1/2002 | Barrett |
| 6,428,501 B1 | 8/2002 | Reynard |
| 6,520,929 B2 | 2/2003 | Zaleski |
| 6,579,270 B2 | 6/2003 | Sussman et al. |
| 6,902,558 B2 | 6/2005 | Laks |
| 2003/0004455 A1 | 1/2003 | Kadziauska et al. |
| 2003/0069594 A1 | 4/2003 | Rockley et al. |
| 2003/0199883 A1 | 10/2003 | Laks |
| 2003/0208218 A1 | 11/2003 | Kadziauskas |
| 2004/0068270 A1 | 4/2004 | Allred |
| 2004/0089080 A1 | 5/2004 | Kadziauskas |
| 2004/0153093 A1 | 8/2004 | Donovan |
| 2005/0234473 A1 | 10/2005 | Zacharias |
| 2005/0256462 A1 | 11/2005 | Underwood |
| 2010/0121260 A1 | 5/2010 | Ghannoum et al. |

OTHER PUBLICATIONS

Holland, Edward J., "Acrysof Toric IOL: Surgical Pearls," Cataract & Refractive Surgery Today, Nov./Dec. 2006, pp. 56-57.

* cited by examiner

PATCH FOR IRRIGATION/ASPIRATION TIP

FIELD OF THE INVENTION

The present invention generally pertains to ophthalmic surgery. More particularly, but not by way of limitation, the present invention pertains to instruments and methods for removing cataracts.

DESCRIPTION OF THE RELATED ART

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age, disease, trauma, etc. causes the lens to become less transparent, vision deteriorates because of the diminished light which can be transmitted to the retina. This deficiency in the lens of the eye is medically known as a cataract. A generally accepted treatment for this condition is surgical removal and replacement of the lens with an artificial intraocular lens (IOL).

SUMMARY OF THE INVENTION

In various embodiments, an ophthalmic surgical instrument may include an aspiration tube defining an aspiration channel, having a proximal end and a distal end, an irrigation/aspiration tip, formed of a first material (e.g., plastic), coupled to and conforming to the distal end of the aspiration tube, and a patch, coupled to the irrigation/aspiration tip, made of a second material (e.g., silicone) having a higher coefficient of friction than the first material. Other materials for the first and second material are also contemplated. In some embodiments, the patch may be placed on the irrigation/aspiration tip in a position to allow a user of the irrigation/aspiration tip to manipulate an intraocular lens (IOL) through contact between the patch and the IOL. For example, the patch may be positioned on a side of the irrigation/aspiration tip opposite an aspiration port or on a distal end of the irrigation/aspiration tip. In some embodiments, the patch may be formed separately and coupled to the irrigation/aspiration tip through an adhesive or may be molded directly onto the irrigation/aspiration tip. In some embodiments, the patch may include one or more features to increase friction between the patch and the IOL.

BRIEF DESCRIPTION OF THE DRAWINGS

For a more complete understanding of the present invention, reference is made to the following description taken in conjunction with the accompanying drawings in which.

It is to be understood that both the foregoing general description and the following detailed description are exemplary and explanatory only and are intended to provide a further explanation of the present invention as claimed.

DETAILED DESCRIPTION OF THE EMBODIMENTS

Incorporation by Reference

U.S. patent application entitled "DISTAL PLASTIC END INFUSION/ASPIRATION TIP," Ser. No. 12/269,373, by Ziad R. Ghannoum and Glenn Sussman filed Nov. 12, 2008 is hereby incorporated by reference in its entirety as though fully and completely set forth herein.

Previously, to remove a lens from an eye, surgical personnel sometimes used an ophthalmic instrument with an infusion sleeve and an aspiration tube therein. Surgical personnel also used a sleeve made of silicon and having a hole therein for aspirating fluid. Surgical personnel slipped the sleeve over the aspiration tube and then used the instrument for ophthalmic surgery. The sleeves, though, were often difficult to use. For instance, the sleeves could tear thereby making it necessary to remove and replace the damaged sleeve. In addition, once on the aspiration tube, these sleeves could slip off of the aspiration tube making its replacement on the aspiration tube necessary. Moreover, because these sleeves only partially filled the space between the aspiration tube and the infusion tube, some infusion fluid could leak out of the distal end of the instrument and move in a forward direction and into the eye. This condition may be undesirable because surgical personnel typically prefer that the instrument direct the infusion fluid perpendicularly from the instrument while aspirating material longitudinally from the distal end of the instrument.

Figure 1:
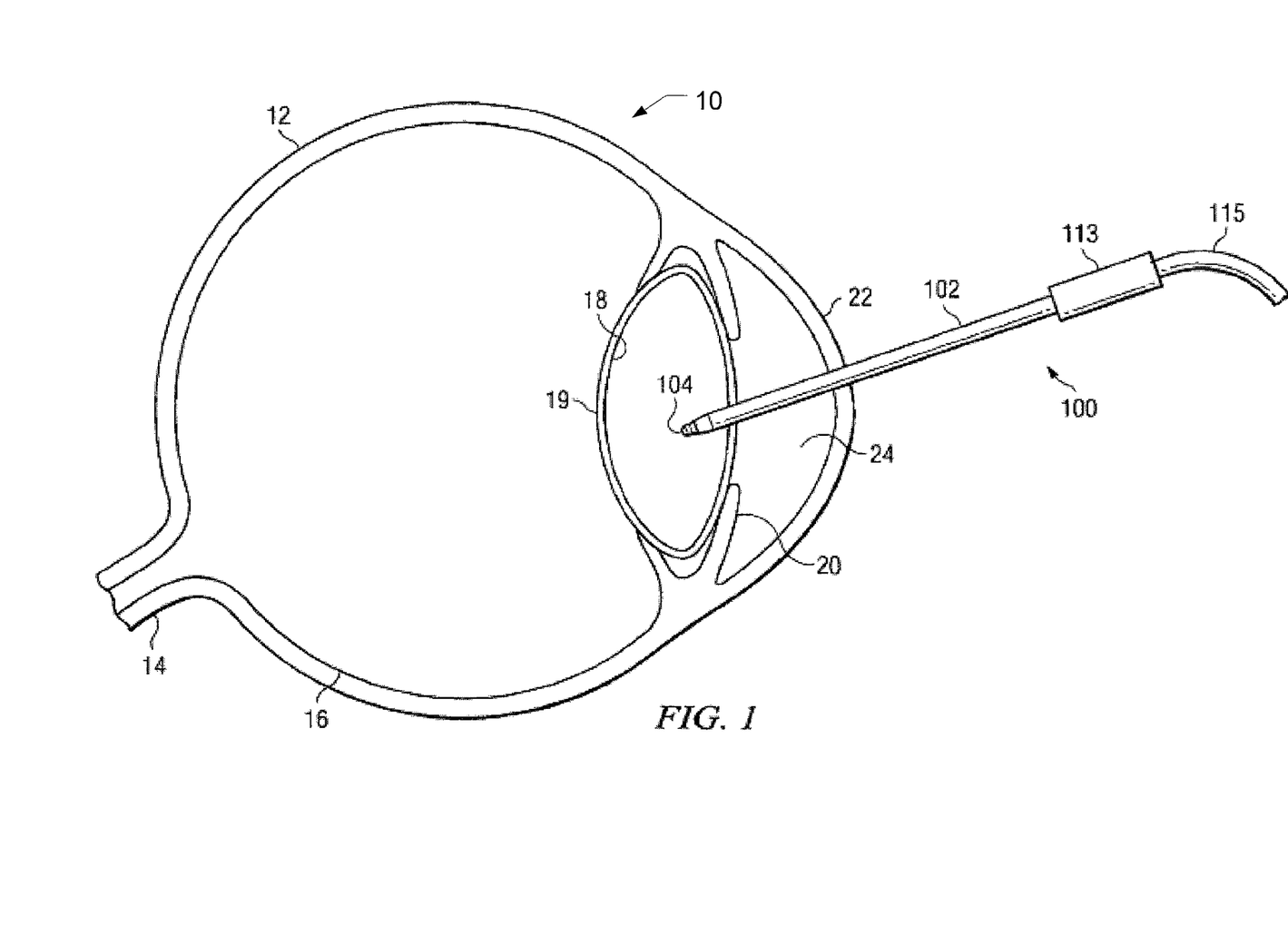
FIG. 1 illustrates a cross sectional view of an eye undergoing ophthalmic surgery.

With reference now to FIG. 1, a cross sectional view of eye 10 undergoing ophthalmic surgery is illustrated. The procedure illustrated could be a cataract extraction. Eye 10 includes sclera 12, optic nerve 14, retina 16, lens 18, capsular bag 19, iris 20, cornea 22, and pupil 24. Normally, lens 18 focuses light passing through cornea 22 and pupil 24 on to retina 16. Retina 16 converts light to nerve impulses which retina 16 sends along optic nerve 14 to the brain. Iris 20 regulates the amount of light passing through pupil 24 and lens 18 thereby allowing eye 10 to adapt to varying levels of light. Capsular bag 19 holds lens 18 in place and is transparent so that light may pass through it. Thus, the nerve impulses traveling along optic nerve 14 correspond to scenes visible to eye 10.

However, various diseases, conditions, injuries, etc. may cause lens 18 to become clouded, translucent, etc. to the point that it might be desirable to extract lens 18 from eye 10. In such situations, the affected patient may be said to have a "cataract." Often, when lens 18 is removed from eye 10 (i.e., the cataract is extracted), surgical personnel replace lens 18 with an artificial lens, thereby restoring sight to the affected patient. Alcon Laboratories, Inc. (of Fort Worth, Tex.) provides exemplary artificial lenses such as the AcrySof® intraocular lenses. To remove lens 18, surgical personnel may use instrument 100. As illustrated by FIG. 1, instrument 100 may include elongated infusion sleeve 102, infusion/aspiration tip 104, and handpiece 113. Ophthalmic tubing 115 may be connected to instrument 100 at handpiece 113 and may supply infusion fluid from an infusion/aspiration machine to instrument 100 and return material aspirated from eye 10 to the infusion/aspiration machine. Handpiece 113 may provide communication channels between ophthalmic tubing 115 and infusion sleeve 102 and infusion/aspiration tip 104. Additionally, handpiece 113 may couple with infusion sleeve 102 and indirectly with infusion/aspiration tip 104 (via one or more internal components) thereby holding these components 102 and 104 in fixed operational relationship to each other.

To extract the cataract, surgical personnel may make an incision in cornea 22 and capsular bag 19. Through the incision, surgical personnel may insert infusion/aspiration tip 104 of instrument 100 into lens 18. Using instrument 100, surgical personnel may direct infusion fluid from infusion/aspiration tip 104 into lens 18 thereby causing lens 18 to disintegrate. Infusion/aspiration tip 104 may draw the infusion fluid, cortical material, and portions of disintegrated lens 18 from capsular bag 19. At some time, surgical personnel may withdraw instrument 100 from eye 10, insert an artificial lens into capsular bag 19 of eye 10, and close the incision.

Previously, during such procedures, micro burrs on surfaces of previously available instruments would catch on, and tear, capsular bag 19. Furthermore, forward leakage of infusion fluid from previously available instruments could interfere with aspiration of material from capsular bag 19. Forward leakage may reduce the efficiency of various surgical techniques and increase the time necessary for performing such techniques. Embodiments of instrument 100, though, may have a smooth, relatively micro burr-free, surfaces. Thus, embodiments of instrument 100 may reduce, if not eliminate, capsular bag 19 tears caused by micro burrs while increasing the speed and efficiency of various ophthalmic techniques.

Figure 2:
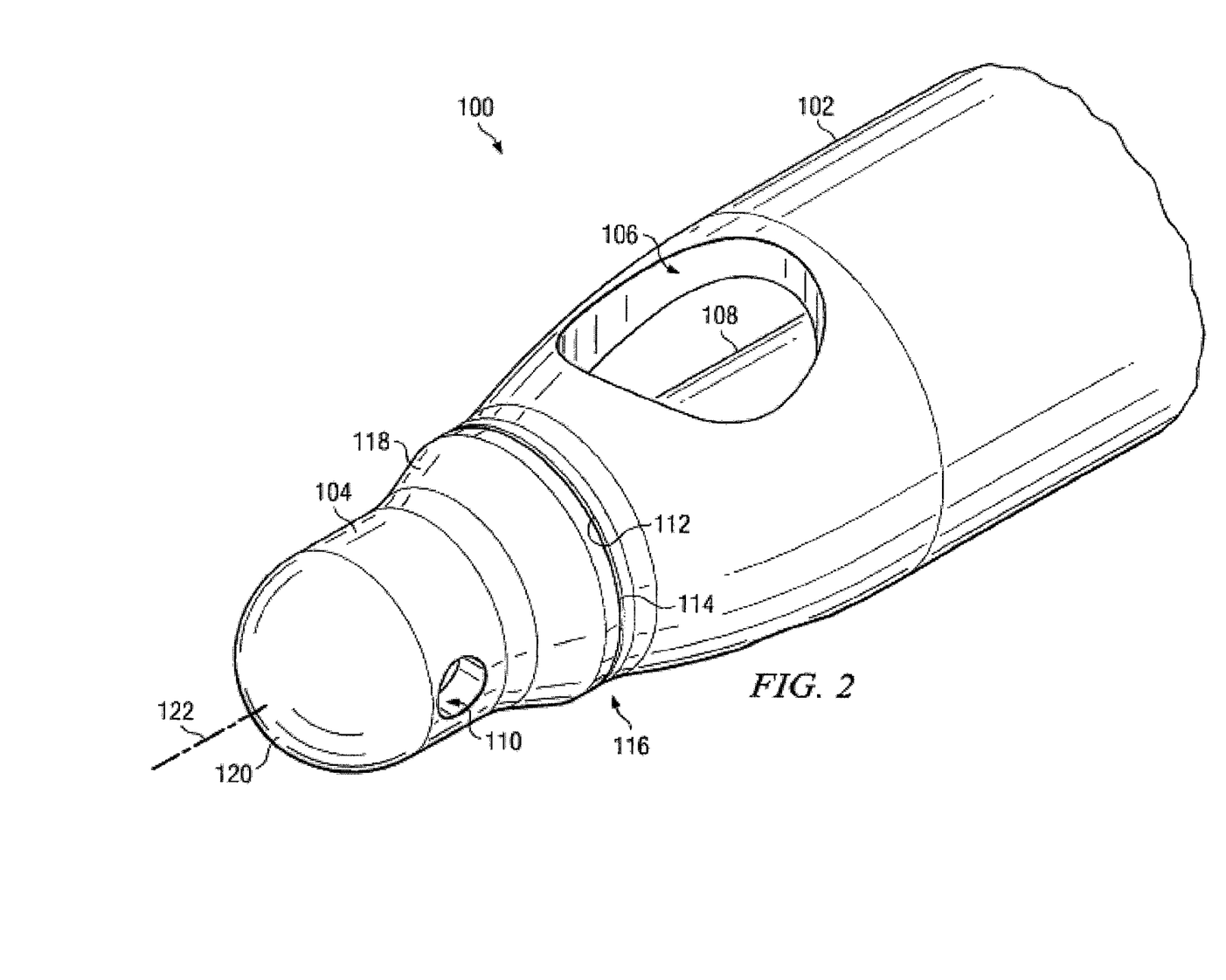
FIG. 2 illustrates a perspective view of an ophthalmic surgical instrument, according to an embodiment.

FIG. 2 further illustrates instrument 100 including infusion sleeve 102, infusion/aspiration tip 104, infusion port 106, aspiration tube 108, aspiration port 110, distal end 112 of infusion sleeve 102, flange 114 of infusion/aspiration tip 104, proximal end 116 of infusion/aspiration tip 104, tapered portion 118 of infusion/aspiration tip 104, distal end 120 of infusion/aspiration tip 104, and longitudinal axis 122 of instrument 100. Aspiration tube 108 may fit coaxially within infusion sleeve 102 and both may couple to handpiece 113 (see FIG. 1) at their respective proximal ends. Handpiece 113 may provide communication paths from ophthalmic tubing 115 (see FIG. 1) to and from, respectively, infusion sleeve 102 and aspiration tube 108. Thus, infusion fluid may be directed distally through infusion sleeve 102 and out through infusion port 106 in a direction perpendicular to longitudinal axis 122. Aspiration port 110 of infusion/aspiration tip 104 may draw material from its environment (for instance, lens 18 of FIG. 1) for return to, for example, an infusion/aspiration machine via aspiration tube 108. The direction from which aspiration port 110 may draw material may be perpendicular to the direction in which infusion port 106 directs fluid.

Figure 3:
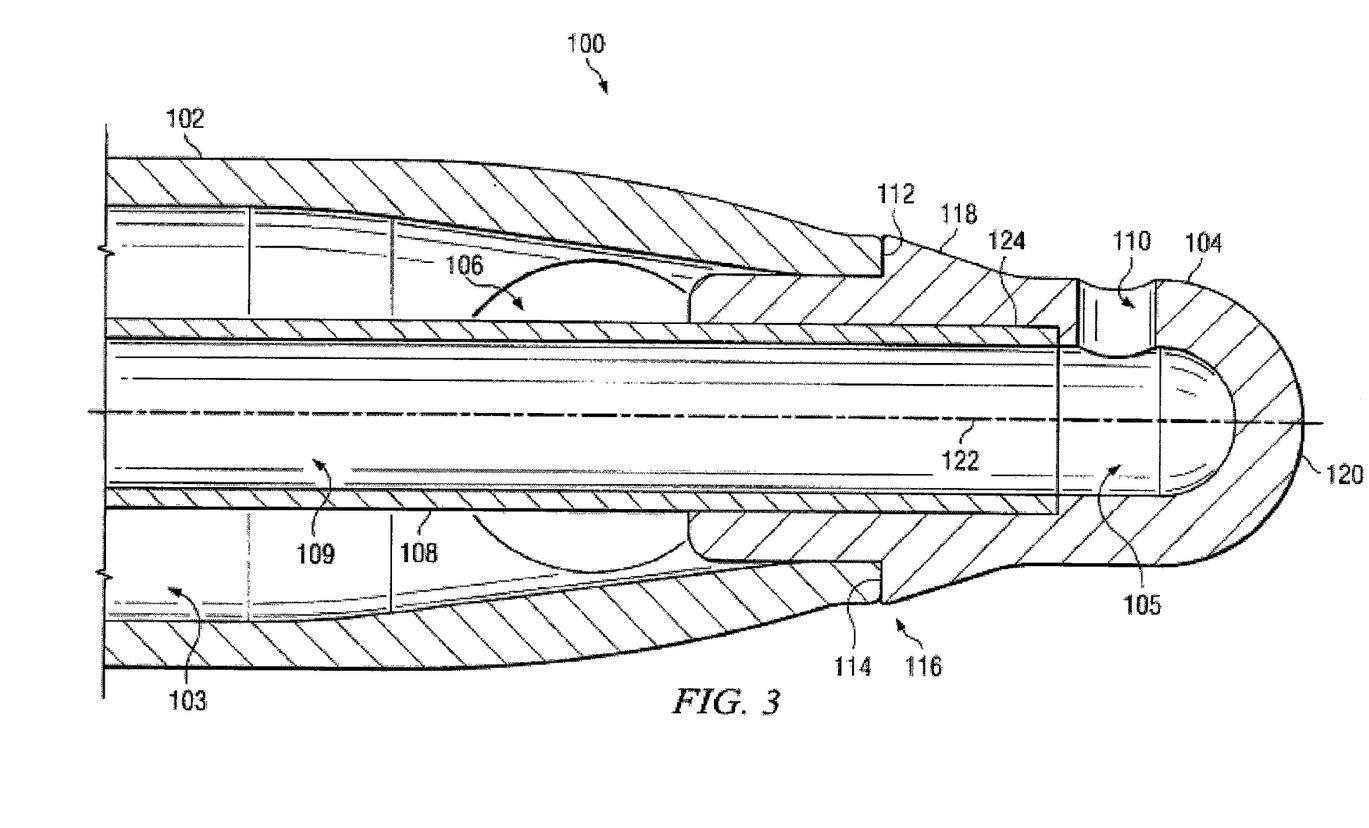
FIG. 3 illustrates a cross sectional view of one embodiment of an ophthalmic surgical instrument.

FIG. 3 illustrates a cross sectional view of one embodiment of instrument 100. Furthermore, FIG. 3 illustrates infusion sleeve 102; infusion channel 103; irrigation/aspiration tip 104; aspiration channel 105; infusion port 106; aspiration tube 108; aspiration channel 109; aspiration port 110; distal end 112 of infusion sleeve 102; flange 114; proximal end 116 of infusion/aspiration tip 104; tapered portion 118; distal end 120 of infusion/aspiration tip 104; longitudinal axis 122; and distal end 124 of aspiration tube 108. More particularly, FIG. 3 illustrates infusion/aspiration tip 104 being coupled to and conforming to distal end 124 of aspiration tube 108. In some embodiments, infusion/aspiration tip 104 may be overmolded onto aspiration tube 108. Aspiration channel 105 of infusion/aspiration tip 104 may align with and correspond to aspiration channel 109 of aspiration tube 108. In some embodiments, aspiration channel 105 of infusion/aspiration tip 104 may extend distally beyond aspiration port 110. Aspiration channel 105 of infusion/aspiration tip 104 may communicate with aspiration port 110 thereby allowing instrument 100 to aspirate material generally adjacent to infusion/aspiration tip 104 through aspiration port 110, aspiration channel 105 of infusion/aspiration tip 104, and aspiration channel 109 of aspiration tube 108 (and then through ophthalmic tubing 115 for disposal). From aspiration channel 109 of aspiration tube 108, aspirated material may be returned to an infusion/aspiration machine (or other system for disposal) via ophthalmic tubing 115 (see FIG. 1).

Flange 114 of infusion/aspiration tip 104 may abut distal end 112 of infusion sleeve 102 and may seal infusion channel 103 against leakage from distal end 112 of infusion sleeve 102. Infusion/aspiration tip 104 may extend into infusion channel 103 some distance thereby also sealing against the internal walls of infusion sleeve 102. Furthermore, infusion/aspiration tip 104 may extend into infusion sleeve 102 to a point adjacent to a portion of infusion port 106 thereby blocking flow through infusion channel 103 and directing infusion fluid out through infusion port 106. In some embodiments, the interior surface of infusion sleeve 102 may taper away from infusion/aspiration tip 104 in the vicinity of infusion port 106, thereby allowing flow through infusion port 106 passed infusion/aspiration tip 104. In some embodiments, infusion/aspiration tip 104 may be retained in infusion sleeve 102 by friction between infusion/aspiration tip 104 and the internal walls of infusion sleeve 102 despite pressure within infusion channel 103. For instance, infusion/aspiration tip 104 and infusion sleeve 102 may be shaped and dimensioned to create an interference fit when infusion/aspiration tip 104 is inserted into infusion sleeve 102. Alternatively, some clearance may exist between infusion/aspiration tip 104 and infusion sleeve 102. In some embodiments, infusion/aspiration tip 104 may be indirectly coupled to handpiece 113 (see FIG. 1) by aspiration tube 108, thereby allowing it to remain in infusion sleeve 102 despite pressure therein. The indirect coupling of infusion/aspiration tip 104 and handpiece 113 may hold infusion/aspiration tip 104 against distal end 112 of infusion sleeve 102 thereby creating a seal between these two components 104 and 102. Thus, infusion/aspiration tip 104 may prevent leakage of infusion fluid from infusion sleeve 102 in a direction along longitudinal axis 122.

FIG. 3 also illustrates infusion/aspiration tip 104 including tapered portion 118. Tapered portion 118 may have a diameter at proximal end 116 of infusion/aspiration tip 104 which is about the same as the diameter of distal end 112 of infusion sleeve 102. Thus, the profile of infusion/aspiration tip 104 may correspond to the profile of infusion sleeve 102. Tapered portion 118 may taper to another, smaller diameter some distance from proximal end 116 of infusion/aspiration tip 104. Thus, the interface between infusion/aspiration tip 104 and infusion sleeve 102 may be smooth and offer little or no resistance to inserting instrument 100 into eye 10 (see FIG. 1). From the distal end of tapered portion 118, the surface of infusion/aspiration tip 104 may be parallel to longitudinal axis 122 from approximately tapered portion 118 to approximately the distal edge of aspiration port 110.

Infusion/aspiration tip 104 may be formed from various plastics, elastomers, etc. while infusion sleeve 102 and aspiration tube 108 may be formed from stainless steel (e.g., a 304 SS Hypo Tube), titanium, or any other biocompatible material. In some embodiments, infusion/aspiration tip 104 may be made from a plastic material such as a polycarbonate (e.g., Makrolon® 2558 which is available from Bayer MaterialScience L.L.C. of Pittsburg, Pa.)). Thus, infusion/aspiration tip 104 may have a smooth surface free of sharp edges, micro burrs, etc. Accordingly, infusion/aspiration tips 104 of various embodiments may avoid tearing capsular bag 19, thereby speeding patient recovery and reducing patient discomfort associated with certain ophthalmic surgical procedures.

Moreover, instrument 100 may be quickly assembled by surgical personnel. Instrument 100 may be assembled by sliding aspiration tube 108 (with infusion/aspiration tip 104 overmolded thereon) into infusion sleeve 102. As infusion/aspiration tip 104 approaches distal end 112 of infusion sleeve 102, surgical personnel may align infusion/aspiration tip 104 and distal end 112 of infusion sleeve 102. Surgical personnel may push infusion/aspiration tip 104 into infusion channel 103 thereby sealing distal end 112 of infusion sleeve 102. Surgical personnel may, when desired, connect infusion sleeve 102 and aspiration tube 108 to handpiece 113, ophthalmic tubing 115, etc. (see FIG. 1).

Surgical personnel may navigate instrument 100 to the vicinity of eye 10 and begin to insert distal end 120 of infusion/aspiration tip 104 into an incision therein. As infusion/aspiration tip 104 enters eye 10, smooth surfaces of infusion/aspiration tip 104 may distract tissues it encounters without tearing capsular bag 19 or otherwise traumatizing eye 10. As surgical personnel advance instrument 100 into eye 10, tapered portion 118 may also distract tissues without tearing capsular bag 19 or otherwise traumatizing eye 10. Surgical personnel may therefore manipulate instrument 100 to extract cataracts and other tissues as may be desired. When desired, surgical personnel may withdraw instrument 100 from eye 10.

Surgical personnel may disassemble instrument 100 and dispose of infusion/aspiration tip 104 and aspiration tube 108. Infusion/aspiration tip 104 and aspiration tube 108 may be relatively inexpensive to manufacture thereby allowing such single uses of infusion/aspiration tip 104 and aspiration tube 108. Thus, embodiments may alleviate surgical personnel from the need to clean and sterilize infusion/aspiration tip 104 and aspiration tube 108 following various surgical procedures. Moreover, because infusion/aspiration tip 104 and aspiration tube 108 may be pre-sterilized, the need for surgical personnel to clean and sterilize infusion/aspiration tip 104 and aspiration tube 108 (including any crevice that might exist between infusion sleeve 102 and infusion/aspiration tip 104) prior to certain ophthalmic surgical procedures may be alleviated by various embodiments.

Figure 4:
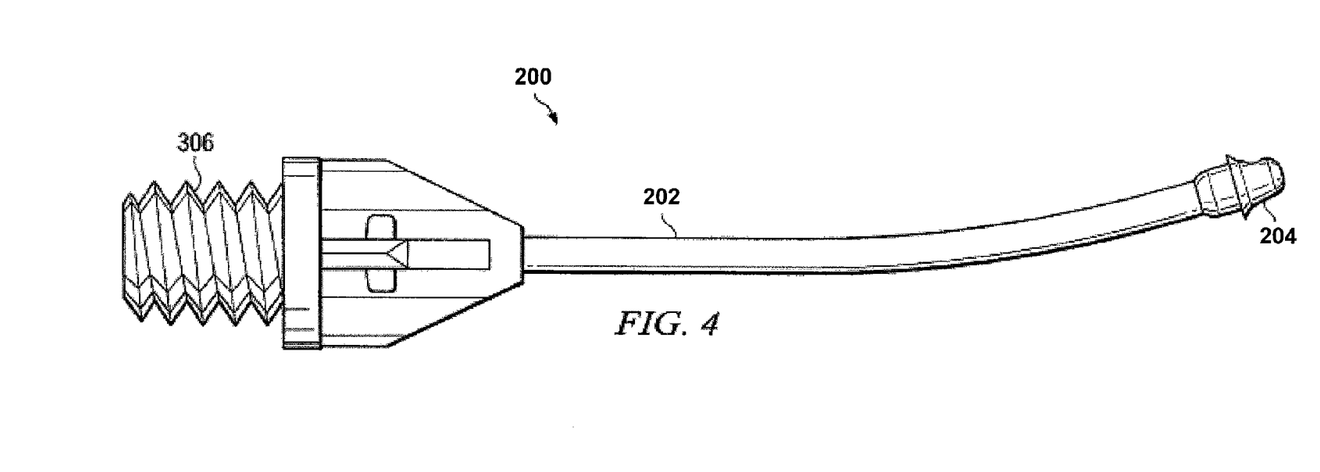
FIG. 4 illustrates a diagrammatic representation of a curved ophthalmic instrument, according to an embodiment.
Figure 5:
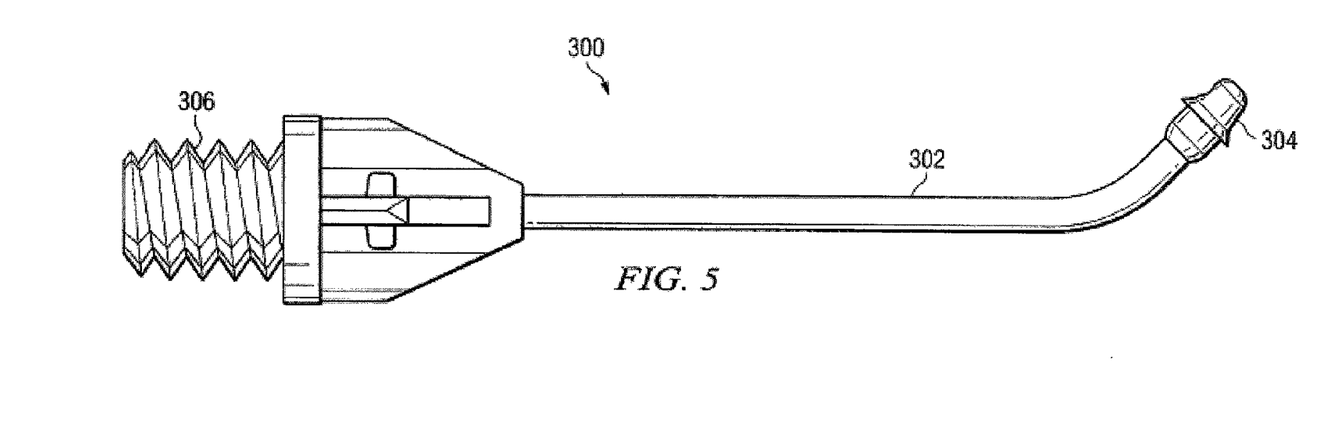
FIG. 5 illustrates a diagrammatic representation of a bent ophthalmic instrument, according to an embodiment.

In some embodiments, surgical instrument 300 may have a curved profile (e.g., see FIG. 4). In FIG. 4, instrument 200 may include aspiration sleeve 202, infusion/aspiration tip 204, and an attachment portion 306 for attachment to a hand piece. The radius of curvature of aspiration tube 202 may be selected to extend the entire length of aspiration tube 202 or a portion of the length. One or more sections of aspiration tube 202 may remain straight when the tube is curved. As shown in FIG. 5, the curved section may be relatively small and have a small radius, while the remainder of aspiration tube 302 remains straight to give the instrument 300 a bent appearance. For example a straight portion may run from attachment portion 306 to the curved section and another straight portion may run from the curved section to infusion/aspiration tip 304. In other embodiments, a bent profile may be achieved using a non-curved interface between straight sections.

Figure 6A:
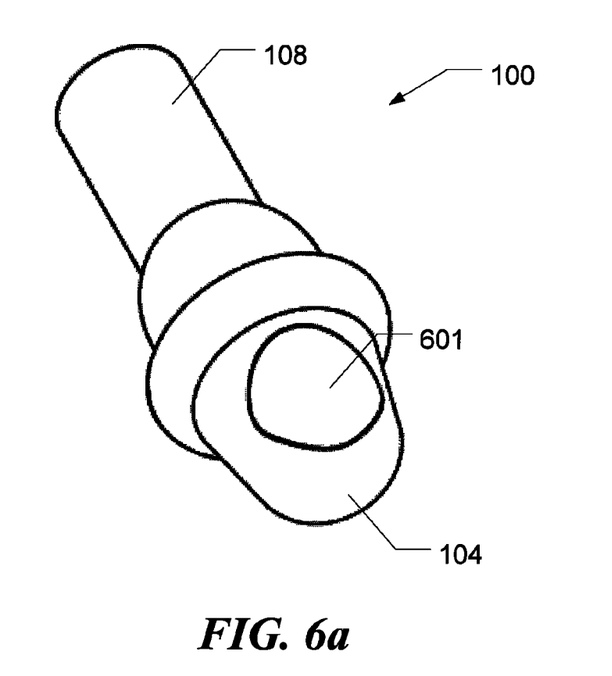
FIGS. 6a-f illustrate various views of a patch for the ophthalmic instrument, according to an embodiment.
Figure 6B:
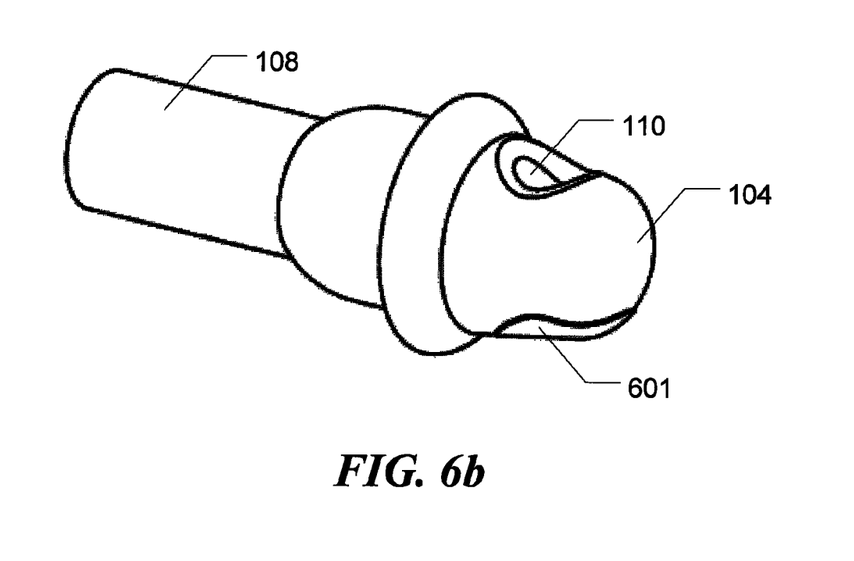
Figure 6C:
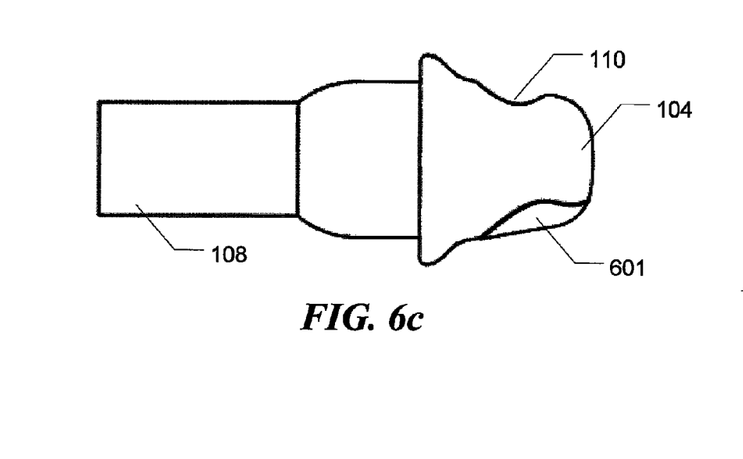
Figure 6D:
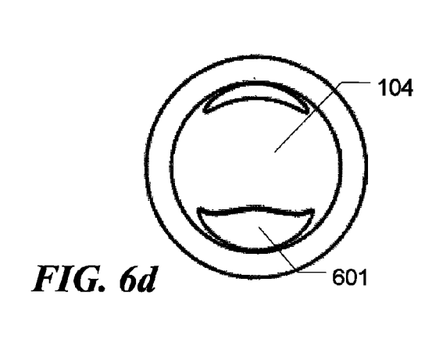
Figure 6E:
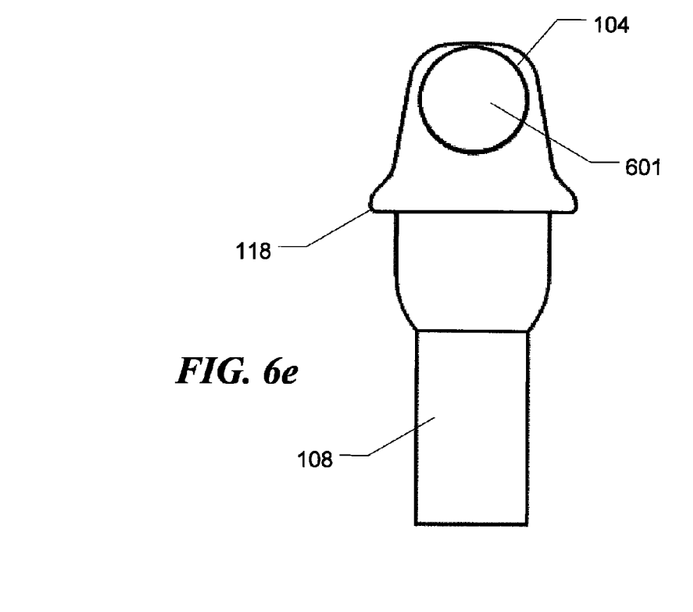
Figure 6F:
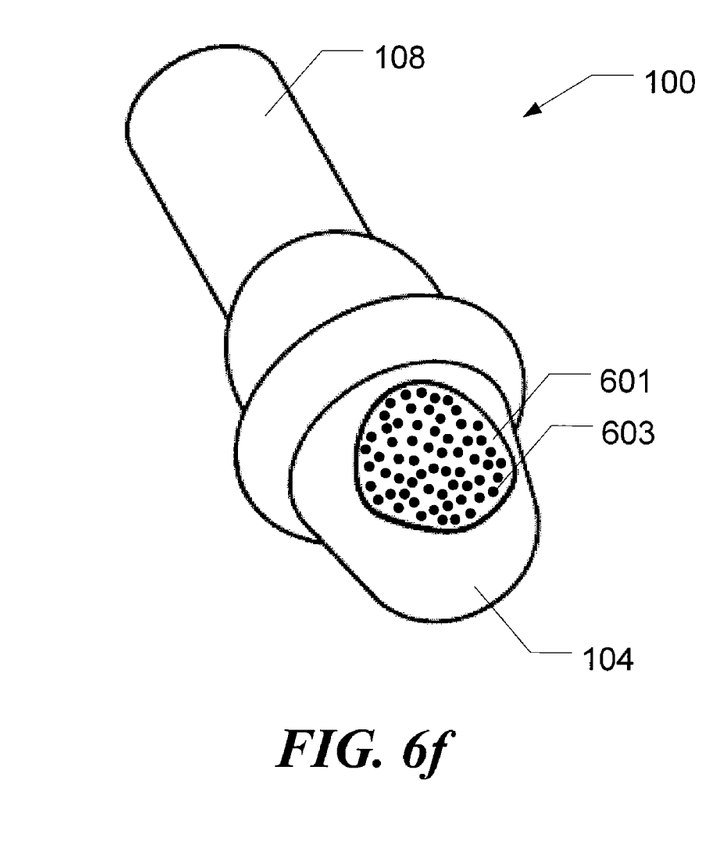
Figure 7:
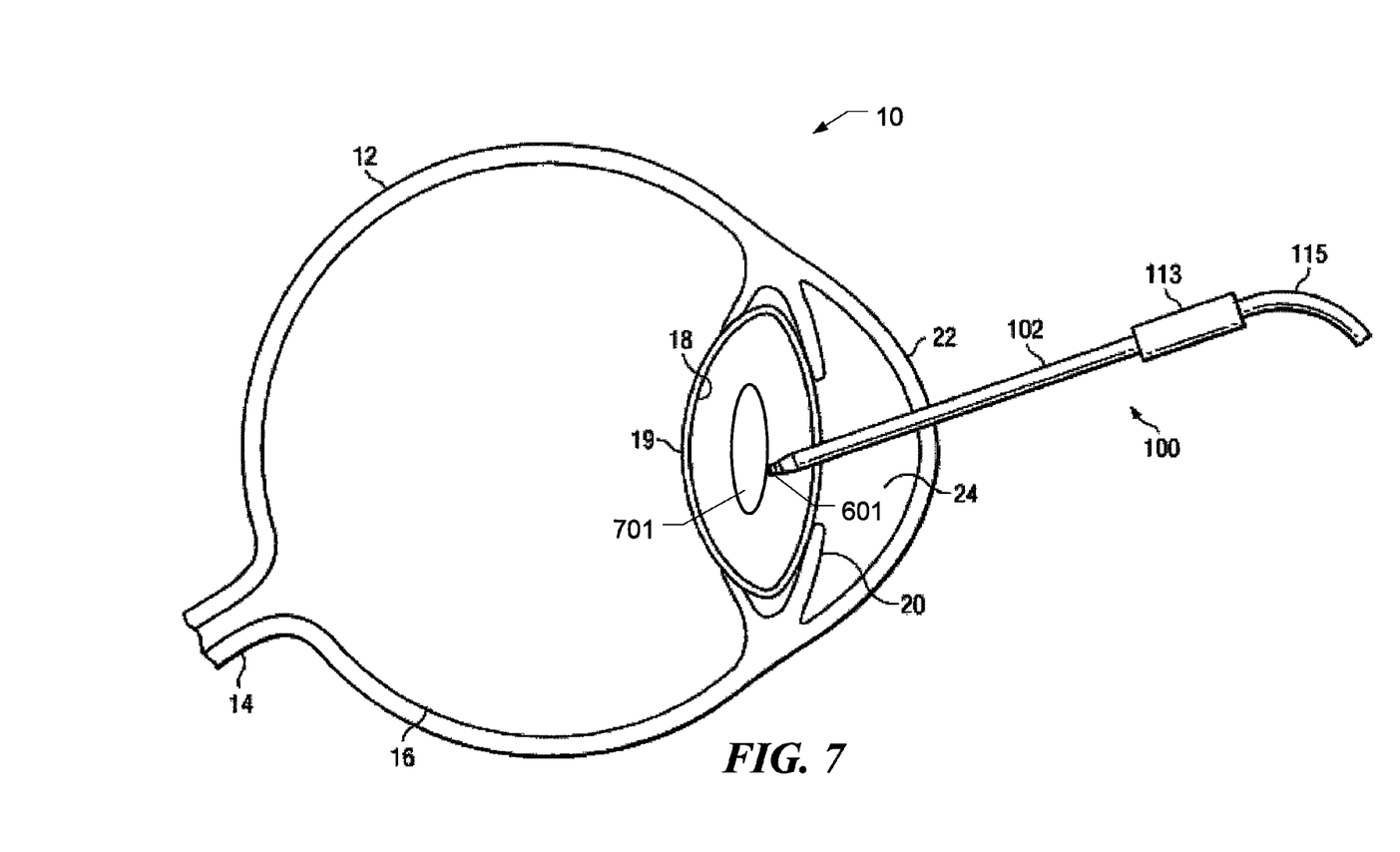
FIG. 7 illustrates a view of the ophthalmic instrument with a patch engaging an intraocular lens (IOL) inside a capsular bag, according to an embodiment.

FIGS. 6a-f illustrate various views of an embodiment of a patch 601 for the ophthalmic instrument. In some embodiments, the surgical instrument 100 may be used after a cataract removal procedure for cortical clean-up. An embodiment of the irrigation/aspiration tip 104 attached to aspiration tube 108 is shown with a patch 601. As seen in FIG. 7, the patch 601 may be used by a surgeon to manipulate (e.g., move, orient, etc.) an intraocular lens (IOL) 701 inside the capsular bag 19. In some embodiments, the patch 601 may be made of silicone or another material that provides friction between the patch 601 and the IOL 701 to facilitate such manipulation through patch 601 on IOL 701 contact. The irrigation/aspiration tip 104 may be made from a polycarbonate or other material with a low coefficient of friction that does not easily engage the IOL 701. The patch 601 may be made of a material (such as silicone) with a higher coefficient of friction that will provide a gripping surface for gripping the IOL 701 (through friction between the patch surface and the IOL 701). Other materials for the patch 601 are also possible (e.g., rubber, latex, etc). As seen in FIG. 6f, in some embodiments, the patch 601 may include features 603 to enhance grip between the patch 601 and the IOL 701. For example, raised bumps, hooks, etc. may be manufactured into the patch 601. In some embodiments, the patch 601 may be made of the same material as the irrigation/aspiration tip 104 and these features may provide the increased friction for IOL 701 manipulation. In some embodiments, the patch 601 may be made of a different material than the irrigation/aspiration tip 104 (such as silicone) and also include these features.

In some embodiments, the patch 601 may be formed separately (e.g., through injection or cast molding) and coupled to the irrigation/aspiration tip 104 through an adhesive. In some embodiments, the patch 601 may be molded directly onto the irrigation/aspiration tip 104 (e.g., molded into a recess in the irrigation/aspiration tip 104). For example, the patch 601 may be inserted partially into the aspiration port 110 or another recess on the tip 104 to secure the patch 601 to the tip 104. Other manufacturing techniques are also possible. For example, the patch 601 may be formed by placing a patch of silicone gel onto the irrigation/aspiration tip 104. In some embodiments, the patch 601 may have a round configuration as shown in FIGS. 6a-f. For example, the patch 601 may have a diameter approximately in a range of 0.2 mm to 1 mm. Other shapes are also contemplated (e.g., rectangular, square, elliptical, irregular, etc). Other dimensions are also contemplated (e.g., larger or smaller diameters based on the type of tip the patch 601 is applied to).

In some embodiments, the patch 601 may be placed on a side of the irrigation/aspiration tip 104 opposite the aspiration port 110 as shown in FIG. 6b. Other placements are also contemplated (e.g., on the distal end 120 of irrigation/aspiration tip 104). While the embodiment in FIGS. 6a-f is described with reference to irrigation/aspiration tip 104 for surgical instrument 100, the patch 601 may also be used on irrigation/aspiration tips 204 and 304 of surgical instruments 200 and 300, respectively. In some embodiments, the patch 601 may have a different color (e.g., blue, bright orange, etc.) than the irrigation/aspiration tip 104 (which may, for example, be gray) to assist the surgeon in visually locating the patch 601 when the tip 104 is inserted into the eye 10.

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An ophthalmic surgical instrument, comprising:
   an aspiration tube defining an aspiration channel, having a proximal end and a distal end;

an irrigation/aspiration tip, formed of a first material, coupled to the distal end of the aspiration tube, wherein the irrigation/aspiration tip has a closed distal end and has at least one external aspiration port, entirely on a first side of the irrigation/aspiration tip, in fluid communication with and forming an outermost portion of the aspiration channel; and a patch coupled to the irrigation/aspiration tip, wherein the patch is made of a second material having a higher coefficient of friction than the first material, wherein the patch is entirely on a second side of the irrigation/aspiration tip to allow a user of the irrigation/aspiration tip to manipulate an intraocular lens (IOL) through contact between the patch and the IOL;

wherein the first side of the irrigation/aspiration tip lies entirely on one spatial side of a plane containing a longitudinal axis of the tip and the second side lies entirely on the opposing spatial side of the plane.

2. The ophthalmic surgical instrument of claim 1, wherein the first material is a plastic and the second material is silicone.

3. The ophthalmic surgical instrument of claim 1, wherein the second side of the irrigation/aspiration tip is opposite the first side of the irrigation/aspiration port.

4. The ophthalmic surgical instrument of claim 1, wherein the patch is a different color than the irrigation/aspiration tip.

5. The ophthalmic surgical instrument of claim 1, wherein the patch is formed separately and coupled to the irrigation/aspiration tip through an adhesive.

6. The ophthalmic surgical instrument of claim 1, wherein the patch is molded onto the irrigation/aspiration tip.

7. The ophthalmic surgical instrument of claim 1, wherein the patch comprises one or more features to increase friction between the patch and the IOL.

8. The ophthalmic surgical instrument of claim 1, wherein an exposed outer surface area of the patch is less than half of an exposed outer surface area of the irrigation/aspiration tip.

9. An ophthalmic surgical instrument comprising:

an infusion sleeve comprising an elongated body defining an infusion channel and having a proximal end, a distal end, and a longitudinal axis along the length of the elongated body, the infusion sleeve defining an infusion port oriented to direct infusion fluid from the infusion channel in a first direction which is perpendicular to the longitudinal axis;

an aspiration tube defining an aspiration channel, having a proximal end and a distal end;

an irrigation/aspiration tip, formed of a first material, coupled to the distal end of the aspiration tube, wherein the irrigation/aspiration tip has a closed distal end and has at least one external aspiration port, entirely on a first side of the irrigation/aspiration tip, in fluid communication with and forming an outermost portion of the aspiration channel;

wherein the external aspiration port of the irrigation/aspiration tip is oriented to draw material from the environment in a second direction which is perpendicular to the longitudinal axis, and wherein the irrigation/aspiration tip extends in a direction along the longitudinal axis; and a patch coupled to the irrigation/aspiration tip, wherein the patch is made of a second material having a higher coefficient of friction than the first material, wherein the patch is entirely on a second side of the irrigation/aspiration tip to allow a user of the irrigation/aspiration tip to manipulate an intraocular lens (IOL) through contact between the patch and the IOL;

wherein the first side of the irrigation/aspiration tip lies entirely on one spatial side of a plane containing a longitudinal axis of the tip and the second side lies entirely on the opposing spatial side of the plane.

10. The ophthalmic surgical instrument of claim 9, wherein the first material is a plastic and the second material is silicone.

11. The ophthalmic surgical instrument of claim 9, wherein the second side of the irrigation/aspiration tip is opposite the first side of the irrigation/aspiration port.

12. The ophthalmic surgical instrument of claim 9, wherein the patch is a different color than the irrigation/aspiration tip.

13. The ophthalmic surgical instrument of claim 9, wherein the patch is formed separately and coupled to the irrigation/aspiration tip through an adhesive.

14. The ophthalmic surgical instrument of claim 9, wherein the patch is molded onto the irrigation/aspiration tip.

15. The ophthalmic surgical instrument of claim 9, wherein the patch comprises one or more features to increase friction between the patch and the IOL.

16. The ophthalmic surgical instrument of claim 9, wherein an exposed outer surface area of the patch is less than half of an exposed outer surface area of the irrigation/aspiration tip.

17. A single use, disposable component to be coupled to an ophthalmic surgical instrument wherein the instrument includes an infusion sleeve comprising an elongated body defining an infusion channel and having a proximal end, a distal end, and a longitudinal axis along a length of the elongated body, the component comprising:

an aspiration tube defining an aspiration channel, having a proximal end and a distal end;

an irrigation/aspiration tip, formed of a first material, coupled to the distal end of the aspiration tube, wherein the irrigation/aspiration tip has a closed distal end and has at least one external aspiration port, entirely on a first side of the irrigation/aspiration tip, in fluid communication with and forming an outermost portion of the aspiration channel; and a patch coupled to the irrigation/aspiration tip, wherein the patch is made of a second material having a higher coefficient of friction than the first material, wherein the patch is entirely on a second side of the irrigation/aspiration tip to allow a user of the irrigation/aspiration tip to manipulate an intraocular lens (IOL) through contact between the patch and the IOL;

wherein the patch does not block or form part of the aspiration channel;

wherein the first side of the irrigation/aspiration tip lies entirely on one spatial side of a plane containing a longitudinal axis of the tip and the second side lies entirely on the opposing spatial side of the plane.

18. The single use, disposable component of claim 17, wherein the irrigation/aspiration tip is formed of a plastic and the patch material is a silicone having a higher coefficient of friction than the irrigation/aspiration tip plastic.

* * * * *

UNITED STATES PATENT AND TRADEMARK OFFICE
CERTIFICATE OF CORRECTION

Page 1 of 1

PATENT NO.       : 8,545,462 B2
APPLICATION NO.  : 12/616544
DATED            : October 1, 2013
INVENTOR(S)      : Ghannoum It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 562 days.

Signed and Sealed this
Nineteenth Day of May, 2015

Michelle K. Lee
*Director of the United States Patent and Trademark Office*